(12) United States Patent
DeSimone et al.

(10) Patent No.: US 6,211,422 B1
(45) Date of Patent: *Apr. 3, 2001

(54) ENZYME CATALYSIS IN CARBON DIOXIDE FLUIDS

(75) Inventors: Joseph M. DeSimone, Chapel Hill; Ruben G. Carbonell, Raleigh; Stephanie A. Crette, Carrboro; Jonathan L. Kendall, Apex, all of NC (US)

(73) Assignees: North Carolina State University, Raleigh; The University of North Carolina at Chapel Hill, Chapel Hill, both of NC (US)

( * ) Notice: Subject to any disclaimer, the term of this patent is extended or adjusted under 35 U.S.C. 154(b) by 0 days.

(21) Appl. No.: 09/352,249

(22) Filed: Jul. 13, 1999

(51) Int. Cl.[7] ........................................ C12P 1/00
(52) U.S. Cl. ........................ 585/16; 435/41; 435/183; 560/217
(58) Field of Search ............................ 585/16; 560/217; 435/183, 41

(56) References Cited

U.S. PATENT DOCUMENTS

| | | | |
|---|---|---|---|
| 5,618,710 | 4/1997 | Navia et al. | 435/174 |
| 5,618,894 | 4/1997 | DeSimone et al. | 526/89 |
| 5,679,737 | * 10/1997 | DeSimone et al. | 528/312 |
| 5,719,039 | * 2/1998 | Dordick et al. | 252/511 |
| 5,739,223 | 4/1998 | DeSimone | 526/89 |
| 5,855,819 | * 1/1999 | DeSimone et al. | 435/41 |
| 6,025,459 | * 2/2000 | DeSimone et al. | 524/529 |

OTHER PUBLICATIONS

Colombo et al.; "Application of structure–based thermodynamic calculations to the rationalization of the enantioselectivity of subtilisin in organic solvents," *Tetrahedron: Asymmetry* 9:1205–1214 (1998).
Govardhan et al.; Extremozymes for industry—from nature and by design,: *Chemistry and Industry* 689–693 (Sep. 4, 1995).
Grim; "New technology for the preparation of peptides and peptidomimetrics," *Pharmaceutical Manufacturing International* 49 (1997).
Grim; "A systems approach to biocatalysis," *Pharmaceutical Manufacturing International* 75–76 (1996).
Grim; "From Kit to Kettle—Screening Kits and Catalysts for Biocatalytic Resolutions," *Specialty Chemicals Production, Marketing and Applications* 16:5 165–168 (Aug. 1996).
Khalaf et al.; "Cross–Linked Enzyme Crystals as Highly Active Catalysts in Organic Solvents," *J. Am. Chem. Soc.* 118:5494–5495 (1996).
Lalonde; "The Preparation of Homochiral Drugs and Peptides Using Cross–Linked Enzyme Crystals," *Chimica OGGI/chemistry today* (Jun. 1995).
Lalonde et al.; "Cross–Linked Crystals of *Candida rugosa* Lipase: Highly Efficient Catalysts for the Resolution of Chiral Esters," *Journal of the American Chemical Society* 117:26 6845–6852 (1995).
Lalonde; "Practical catalysis with enzyme crystals," *Chemtech* 27:2 38 (1997).
Lalonde et al.; "Cross–Linked Enzyme Crystals of Lipases as Catalysts for Kinetic Resolution of Acids and Alcohols," *Methods in Enzymology* 286:443–464 (1997).
Lalonde; "Enzyme Catalysis: Cleaner, Safer, Energy Efficient," *Chemical Engineering* 108–112 (Sep. 1997).
Margolin; "Chirals boost interest in enzyme crystals," *Performance Chemicals* (Apr./May 1994).
Margolin; "Novel crystalline catalysts," *TIBTECH* 14:7 (150) 223–230 (Jul. 1996).
Persichetti et al.; "Cross–Linked Enzyme Crystals (CLECs) of Thermolysin in the Synthesis of Peptides," *Journal of the American Chemical Society* 117:10 2732–2737 (1995).
Persichetti et al.; "*Candida rugosa* Lipase: Enantioselectivity Enhancements in Organic Solvents," *Tetrahedron Letters* 37:36 6507–6510 (1996).
St. Clair et al.; "Cross–Linked Enzyme Crystals as Robust Biocatalysts," *J. Am. Chem. Soc.* 114:18 7314–7316 (1992).
Wang et al.; "An Efficient Synthesis of Chiral Amino Acid and Peptide Alkylamides via CLEC–Subtilisin Catalyzed Coupling and in situ Resolution," *Tetrahedron Letters* 37:30 5317–5320 (1996).

(List continued on next page.)

Primary Examiner—Jacqueline V. Howard
(74) Attorney, Agent, or Firm—Myers Bigel Sibley & Sajovec, P.A.

(57) ABSTRACT

A method for the enzymatic production of a desired product in a liquid or supercritical carbon dioxide fluid. The method comprises: (a) providing a reaction mixture comprising at least one reaction substrate and a crosslinked enzyme crystal catalyst in a liquid or supercritical carbon dioxide fluid; and (b) reacting said substrate with said crosslinked enzyme crystal catalyst in said carbon dioxide fluid to produce said product. The reacting step is typically followed by the step of (c) separating the product from said reaction mixture. The crosslinked enzyme crystal catalyst preferably comprises an enzyme crystal crosslinked with a multifunctional crosslinking agent, said crosslinked enzyme crystal having resistance to exogeneous proteolysis, such that the crosslinked enzyme crystal retains at least about 80 percent of its initial activity after incubation for three hours in the presence of a concentration of Pronase™ protease that causes the soluble uncrosslinked form of the enzyme that is crystallized to form said enzyme crystal that is crosslinked to lose at least about 80 percent of its initial activity under the same conditions. Reaction mixtures useful for carrying out the foregoing method and product mixtures produced by the foregoing method are also disclosed.

55 Claims, 2 Drawing Sheets

OTHER PUBLICATIONS

Wang et al.; "Cross–Linked Crystals of Subtilisin: Versatile Catalyst for Organic Synthesis," *The Journal of Organic Chemistry* 62:11 3488–3495 (1997).

Zmijewski et al.; "Kinetic resolutions: evaluation of a one dimensional E value calculation method using a computer and statistical software," *Tetrahedron Letters* 8:8 1153–1156 (1997).

* cited by examiner

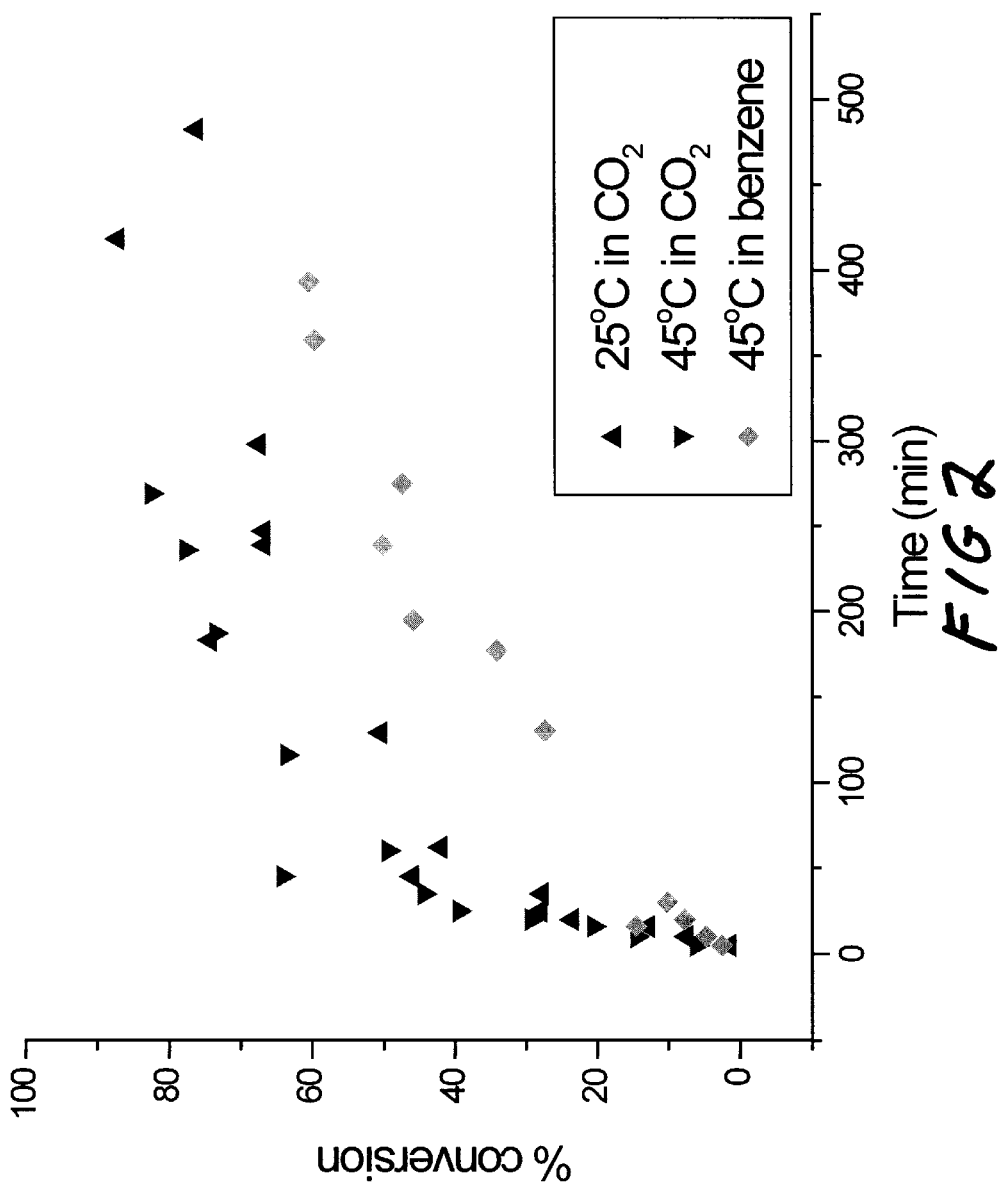

ENZYME CATALYSIS IN CARBON DIOXIDE FLUIDS

FIELD OF THE INVENTION

The present invention concerns enzyme catalysis in carbon dioxide fluids, particularly liquid or supercritical carbon dioxide fluids.

BACKGROUND OF THE INVENTION

Carbon dioxide provides an environmentally friendly solvent system for many reactions. For example, U.S. Pat. No. 5,739,223 to DeSimone describes methods of making fluoropolymers in carbon dioxide systems, U.S. Pat. No. 5,618,894 to DeSimone et al. describes nonaqueous polymerizations of fluoromonomers in carbon dioxide systems, and U.S. Pat. No. 5,679,737 to DeSimone et al. describes heterogeneous polymerizations in carbon dioxide systems.

Unfortunately, carbon dioxide has not provided a useful solvent system for enzyme catalysis. The pH of liquid or supercritical carbon dioxide is typically in the range of 4 to 5, which denatures most proteins or peptides. Hence, it would be extremely desirable to have a means for carrying out enzyme catalysis in liquid or supercritical carbon dioxide.

SUMMARY OF THE INVENTION

In view of the foregoing, a first aspect of the present invention is a method for the enzymatic production of a desired product in a liquid or supercritical carbon dioxide fluid. The method comprises: (a) providing a reaction mixture comprising at least one reaction substrate and a crosslinked enzyme crystal catalyst in a liquid or supercritical carbon dioxide fluid; and (b) reacting said substrate with said crosslinked enzyme crystal catalyst in said carbon dioxide fluid to produce said product. The reacting step is typically followed by the step of (c) separating the product from said reaction mixture.

A second aspect of the present invention is a mixture useful for the enzymatic production of a desired product in carbon dioxide fluid, said mixture comprising:

(a) at least one reaction substrate;
(b) a crosslinked enzyme crystal catalyst (that catalyzes the production of a desired product from said reaction substrate);
(c) liquid or supercritical carbon dioxide fluid; and
(d) optionally, a cosolvent.

A third aspect of the present invention is a mixture comprising the product of the foregoing method, the mixture comprising:

(a) at least one reaction product;
(b) a crosslinked enzyme crystal catalyst (that catalyzes the production of said product from a corresponding reaction substrate);
(c) liquid or supercritical carbon dioxide fluid; and
(d) optionally, a cosolvent.

The foregoing and other objects and aspects of the invention are described in greater detail in the drawings herein and the specification set forth below.

BRIEF DESCRIPTION OF THE DRAWINGS

FIG. 2 shows the transesterification of sec-phenethyl alcohol with vinyl butyrate as a percent conversion in liquid carbon dioxide (25° C. in $CO_2$, pyramids) and supercritical carbon dioxide (45° C. in $CO_2$, inverted pyramids), as compared to 45° C. benzene (diamonds) over an extended time period. Note the greater percent conversions achieved in both liquid and supercritical carbon dioxide as compared to the same reaction carried out in benzene.

DETAILED DESCRIPTION OF PREFERRED EMBODIMENTS

Figure 1:
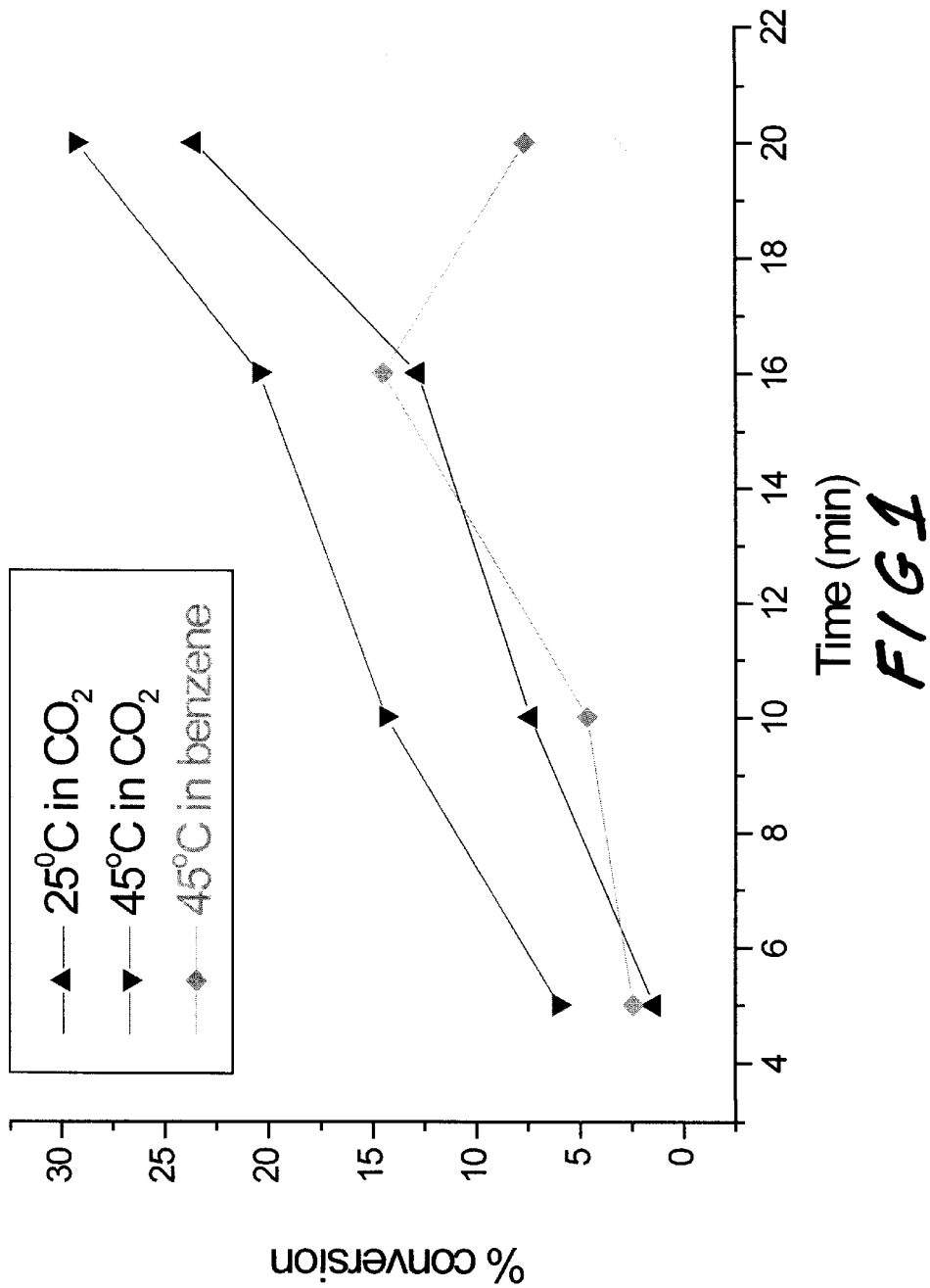
FIG. 1 shows the transesterification of sec-phenethyl alcohol with vinyl butyrate as a percent conversion in liquid carbon dioxide (25° C. in $CO_2$, pyramids) and supercritical carbon dioxide (45° C. in $CO_2$, inverted pyramids), as compared to 45° C. benzene (diamonds) over a time period of twenty minutes.

As noted above, a method for the enzymatic production of a desired product in a liquid or supercritical carbon dioxide fluid comprises: (a) providing a reaction mixture comprising at least one reaction substrate and a crosslinked enzyme crystal catalyst in a liquid or supercritical carbon dioxide fluid; and (b) reacting said substrate with said crosslinked enzyme crystal catalyst in said carbon dioxide fluid to produce said product. The reacting step is typically followed by the step of (c) separating said product from said reaction mixture. The reaction mixture will typically comprise:

(a) from about 0.01 or 0.1 to about 40 or 50 percent by weight of at least one reaction substrate;
(b) from about 0.01 or 0.1 to 40 or 50 percent by weight of a crosslinked enzyme crystal catalyst;
(c) from about 5 or 10 to 60, 80 or 99 percent by weight of liquid or supercritical carbon dioxide fluid; and
(d) from about zero, 0.1 or 1 to about 20, 30 or 40 percent by weight of a cosolvent.

Cosolvents may be including water and/or an organic cosolvents. Organic cosolvents are typically polar or nonpolar hydrocarbon cosolvents, such as alcohols (methanol, ethanol, propanol, butanol, etc.), alkanes such as cyclohexane, ketones, tetrahydrofuran, etc.

The reaction substrate or substrates may be any suitable molecule or molecules depending upon the product sought, including proteins, peptides, and organic molecules. Of course, the substrates will be substrates that are specific for the enzymes found in the crosslinked enzyme crystal catalysts. Crosslinked enzyme crystal catalysts are known and described in U.S. Pat. No. 5,618,710 to Navia et al., the disclosure of which is incorporated herein by reference. A crosslinked enzyme crystal catalyst is, in general, an enzyme crystal crosslinked with a multifunctional crosslinking agent, the crosslinked enzyme crystal having resistance to exogeneous proteolysis, such that the crosslinked enzyme crystal retains at least 80 or 90 percent (e.g., 91 percent) of its initial activity after incubation for three hours in the presence of a concentration of Pronase™ protease that causes the soluble uncrosslinked form of the enzyme that is crystallized to form said enzyme crystal that is crosslinked to lose at least 80 or 90 percent (e.g., 94 percent) of its initial activity under the same conditions. Pronase™ protease is a non-specific protease capable of digesting most proteins to free amino acids, and is commercially available from Calbiochem, LaJolla, Calif. USA). The enzyme:Pronase™ ratio may be 1:40, as described in U.S. Pat. No. 5,618,710. Any suitable crosslinking agent may be employed, as disclosed in U.S. Pat. No. 5,618,710, with glutaraldehyde typically being preferred. Typically, the catalyst is provided in the form of microcrystals, which may have a cross-section of $10^{-1}$ mm or less.

Examples of enzymes that can be provided in the crosslinked enzyme crystal catalysts described above include, but are not limited to, alcohol dehydrogenase, alcohol oxidase, aldolase, alkaline phosphatase, asparaginase, carbonic anhydrase, catalase, creatine kinase, glutaminase, glucose oxidase, β lactamases, lactate dehydrogenase, lipase, luciferase, nitrile hydratase, peroxidase, subtilisin, superoxide dismutase, thermolysin, urease, xylose isomerase, nitrile hydratase and nitrileamidase (for the production of acrylamide from acrylonitrile), amino acid esterase, hydantionases, transaminase, amino acid dehydrogenase, formate dehydrogenase, L aspartase, fumarase, hydantoinase, β-galactosidase, srictodine synthetase, penicillin acylase, penicillin amidase, hydroxysteroid dehydrogenases, etc. In general, all of the enzymes set forth in Table 1 and 2 of U.S. Pat. No. 5,628,710 to Novia and all of the reactions described in Table 2 therein may be used or carried out in conjunction with the present invention.

While the crosslinked enzyme crystal catalysts may be free from a solid support (other than the crystals themselves, which may be considered as a solid support), the crosslinked enzyme crystal catalysts may, if desired, by immobilized on a solid support as a bead, vessel wall, etc. to facilitate subsequent steps of separating the reaction mixture ingredients.

A variety of additional ingredients can optionally be included in the reaction mixture depending upon the particular reaction being carried out. For example, the reaction mixture can include a surfactant, such as a surfactant comprising a $CO_2$-philic group joined to a $CO_2$-phobic group (which $CO_2$-phobic group may be either lipophilic or hydrophilic), which may be surface active for a reaction substrate, a reaction product, or both. The $CO_2$-philic group in the surfactant may be a fluoropolymer or siloxane polymer. Suitable surfactants are described in U.S. Pat. No. 5,679,737 to DeSimone, U.S. Pat. No. 5,858,022 to Romack, and U.S. Pat. Nos. 5,676,705; 5,683,473; and 5,683,977 to Jureller et al., the disclosures of which are incorporated herein by reference. When such surfactants are included, they may be included any suitable amount, such as an amount by weight of from about 0.01, 0.1 or 1 to about about 5, 10, or 20 percent by weight or more of the total mixture.

The reaction mixture typically has an acidic pH of from about 2, 3 or 4 to about 5 or 6, with the reacting step being carried out at the aforesaid pH. The reacting step is typically carried out in a reaction vessel (e.g., a stainless steel pressure vessel), at any suitable temperature and pressure that maintains the carbon dioxide as a liquid or supercritical fluid and provides the desired properties for the reaction. The reaction may be carried out at a temperature of about −50° C. to about 200° C., and is typically carried out a temperature of between about −20° C. to about 100 or 150° C. The reaction may be carried out at a pressure ranging from about 15 psi to about 45,000 psi, and is typically carried out at a pressure of between about 500 psi and about 10,000 psi. Temperatures of at least 20, 25, 30, 35, 40 or 45 degrees C. may be employed. The reaction step may be carried out for a time as little as one to two minutes to a time of one half hour, an hour, or two hours or more, depending upon the particular reaction. While the percentage of substrate converted to product is not critical, the percentage conversion may be from 5 or 10 percent to 50 to 80 percent or more. The reacting step may be carried out batchwise or continuously with thorough mixing of the substrate(s) in an appropriate high pressure vessel system, as desired. The reaction may be a heterogeneous or homogeneous reaction, and may be a single phase or multi-phase reaction. In a preferred embodiment, the reaction is carried out under conditions such that the percent conversion of the substrate is greater than that achieved with the same reaction, carried out at the same temperature, in benzene.

After the reacting step is completed, there is typically left in the reaction vessel a product mixture comprising:

(a) from about 0.01, 0.1 or 1 to about 30 or 50 percent by weight of reaction product;

(b) from about 0.01 or 0.1 to about 40 or 50 percent by weight of a crosslinked enzyme crystal catalyst as described above;

(c) from about 5 or 10 to about 60, 80 or 99 percent by weight of liquid or supercritical carbon dioxide fluid; and (d) from about zero, 0.1 or 1 to about 20, 30 or 40 percent by weight of a cosolvent.

The temperature and pH of the mixture will be as described above until further processing and separating steps are carried out.

Any product of a reaction catalyzed by the crosslinked enzyme crystal catalyst may be produced, including proteins, peptides, organic polymers (e.g., polyacrylamide), and organic compounds (including drugs, antibiotics and the like).

The reaction product may be separated from the mixture by any suitable means, depending upon whether the reaction product is soluble or insoluble in the reaction mixture. For example, for an insoluble product, the separating step may be carried out by filtration, pumping the fluid from the reaction vessel, etc. For a soluble product, the separating step may be carried out by venting the carbon dioxide from the reaction vessel.

The present invention is described in greater detail in the following non-limiting Examples, in which "m" means meters, "mm" means millimeters, "ID" means inside diameter, "mg" means milligrams, "$\mu L$" means microliters, "psi" means pounds per square inch, "GC" means gas chromatography, "MS' means mass spectroscopy, and temperatures are given in degrees Centigrade.

EXAMPLE 1-2

Transesterification of sec-Phenethyl Alcohol in Liquid and Supercritical Carbon Dioxide This example describes enzymatic using cross-linked enzymes crystals in liquid and supercritical carbon dioxide. Crosslinked enzyme crystal catalysts had been described as high enantio- and regio-selective catalysts where crystallinity combined with cross-linking make them highly stable and non-soluble in any solvent.

Transesterification of sec-Phenethyl Alcohol with Vinyl Butyrate in Either Carbon Dioxide or Benzene

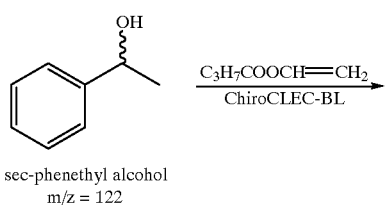

sec-phenethyl alcohol
m/z = 122

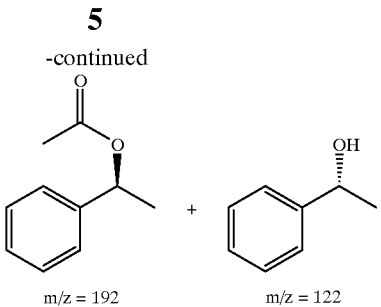

m/z = 192    m/z = 122

The use of a stable catalyst in a non-toxic and environmentally friendly solvent avoids not only toxicity problems related to the use of harsh organic solvents but also any recovery and recycling problems. Thus, the ease of separation and isolation of highly resolved compounds would allow us to kinetically produce a wide range of chiral compounds like drugs, fragrances or food additives. Indeed, different types of crosslinked enzyme crystals are already available to either resolve chiral compounds (Chiro-CLECs™) or synthesize peptides (Pepti-CLECs™).

Materials.

(±)-sec-phenethyl alcohol, S-(−)-sec-phenethyl alcohol, vinyl acetate and vinyl butyrate were purchased from Aldrich. Tetradecane used as a GC standard was purchased from Aldrich. Benzene was distilled and equilibrated on 4 Å molecular sieves before use. Carbon dioxide (SFC/SFE grade) was provided by Air Products and used as received. Cross-linked enzyme crystal catalysts of subtilisin (dry powder, ChiroCLEC™-BL) were purchased from Altus Biologics Inc.

Determination of degree of conversion and of enantiomeric excess.

Both the degree of conversion and the enantiomeric excess of the products obtained in the transesterification reactions were determined by GC/MS with a HP-5MS column (30 m, 0.25 mm ID, HP5890 Series III Gas Chromatograph) and by chiral-GC with a β-dex-120 column manufactured by Supelco.

Transesterification in carbon dioxide.

The transesterification reaction was conducted in a 2.5-mL stainless steel high-pressure view cell containing a magnetic stir bar. The cell was charged with the acylating agent (100 μL of vinyl butyrate), the enzyme (12.5 mg of ChiroCLEC™-BL) and closed. The cell was gradually heated to 45° C. and filled with carbon dioxide to 2700 psi using an ISCO Model No. 260D automatic syringe pump. At the same time, 25 μL of sec-phenethyl alcohol were added to the cell through the $CO_2$ line. At different times, aliquots were withdrawn from the transesterification reaction mixture contained in the high-pressure view cell equipped with a sampling line different from the $CO_2$ filling line. The degree of conversion and the enantiomeric excess of the product determined by GC/MS and chiral-GC. The same transesterification reactions were performed following the same method at room temperature (25° C.) in liquid carbon dioxide.

Crosslinked enzyme crystal catalyzed transesterification in benzene.

To a 5 mL screw-capped vial were added 1 mL of benzene, 2 mg of Chiro-CLEC™-subtilisin and 40 μL of vinyl butyrate. The reaction mixture was stirred at 150 rpm and heated using an oil bath. When the temperature reached to 45° C., 10 μL of sec-phenethyl alcohol were added to the mixture and at different times aliquots were withdrawn. The degree of conversion and the enantiomeric excess of the product determined by GC/MS and chiral-GC Results.

In general, starting material and final product came out well separated onto the GC chromatogram. It has been noticed that after 20 minutes of reaction the degree of conversion was raised if the transesterification was carried out in carbon dioxide rather than in benzene. Futhermore, the degree of conversion was even higher in the case of reactions conducted at 45° C. rather than room temperature.

FIG. 1 shows the transesterification of sec-phenethyl alcohol with vinyl butyrate as a percent conversion in liquid carbon dioxide (25° C. in $CO_2$, pyramids) and supercritical carbon dioxide (45° C. in $CO_2$, inverted pyramids), as compared to 45° C. benzene (diamonds) over a time period of twenty minutes. FIG. 2 shows the transesterification of sec-phenethyl alcohol with vinyl butyrate as a percent conversion in liquid carbon dioxide (25° C. in $CO_2$, pyramids) and supercritical carbon dioxide (45° C. in $CO_2$, inverted pyramids), as compared to 45° C. benzene (diamonds) over an extended time period. Note the greater percent conversions achieved in both liquid and supercritical carbon dioxide, particularly the supercritical carbon dioxide, as compared to the same reaction carried out in benzene.

The transesterification of the racemic mixture gives final products showing an enantiomeric excess determined by chiral GC. The transesterification of (−)-sec-phenethyl alcohol has been performed and allowed us to identify which enantiomer was the fastest to produce the major final product.

The foregoing is illustrative of the present invention, and is not to be construed as limiting thereof. The invention is defined by the following claims, with equivalents of the claims to be included therein.

We claim:

1. A method for the enzymatic production of a product in a liquid or supercritical carbon dioxide fluid, said method comprising:
   (a) providing a reaction mixture comprising at least one substrate and a crosslinked enzyme crystal catalyst in a liquid or supercritical carbon dioxide fluid; and
   (b) reacting said substrate with said crosslinked enzyme crystal catalyst in said carbon dioxide fluid to produce said product.

2. A method according to claim 1, wherein said carbon dioxide fluid comprises liquid carbon dioxide.

3. A method according to claim 1, wherein said carbon dioxide fluid comprises supercritical carbon dioxide.

4. A method according to claim 1, wherein said reaction mixture further comprises a cosolvent.

5. A method according to claim 1, wherein said reacting step is carried out at a pH of from about two to six.

6. A method according to claim 1, wherein said crosslinked enzyme crystal catalyst comprises an enzyme crystal crosslinked with a multifunctional crosslinking agent, said crosslinked enzyme crystal having resistance to exogeneous proteolysis, such that the crosslinked enzyme crystal retains at least about 80 percent of its initial activity after incubation for three hours in the presence of a concentration of Pronase™ protease that causes the soluble uncrosslinked form of the enzyme that is crystallized to form said enzyme crystal that is crosslinked to lose at least about 80 percent of its initial activity under the same conditions.

7. A method according to claim 1, wherein said crystal is a microcrystal.

8. A method according to claim 1, wherein said product is soluble in said reaction mixture.

9. A method according to claim 1, wherein said product is insoluble in said reaction mixture.

10. A method according to claim 1, wherein said reacting step is followed by the step of:
   (c) separating said product from said reaction mixture.

11. A method according to claim 10, wherein said reacting step is carried out in a reaction vessel, and said separating step is carried out by venting said carbon dioxide from said reaction vessel.

12. A mixture useful for the enzymatic production of a product in carbon dioxide fluid, said mixture comprising:
   (a) from about 0.01 to about 50 percent by weight of at least one substrate;
   (b) from about 0.01 to about 50 percent by weight of a crosslinked enzyme crystal catalyst;
   (c) from about 5 to about 99 percent by weight of liquid or supercritical carbon dioxide fluid; and
   (d) from zero to about 30 percent by weight of a cosolvent.

13. A mixture according to claim 12, wherein said carbon dioxide fluid comprises liquid carbon dioxide.

14. A mixture according to claim 12, wherein said carbon dioxide fluid comprises supercritical carbon dioxide.

15. A mixture according to claim 12, and having a pH of from about two to six.

16. A mixture according to claim 12, wherein said crosslinked enzyme crystal catalyst comprises an enzyme crystal crosslinked with a multifunctional crosslinking agent, said crosslinked enzyme crystal having resistance to exogeneous proteolysis, such that the crosslinked enzyme crystal retains at least about 80 percent of its initial activity after incubation for three hours in the presence of a concentration of Pronase™ protease that causes the soluble uncrosslinked form of the enzyme that is crystallized to form said enzyme crystal that is crosslinked to lose at least about 80 percent of its initial activity under the same conditions.

17. A mixture according to claim 12, wherein said crystal is a microcrystal.

18. A mixture according to claim 12, wherein said cosolvent comprises water.

19. A mixture according to claim 12, wherein said cosolvent comprises an organic cosolvent.

20. A mixture produced from the catalytic action of an enzyme on a substrate, said mixture comprising:
   (a) from about 0.01 to about 50 percent by weight of at least one reaction product;
   (b) from about 0.01 to about 50 percent by weight of a crosslinked enzyme crystal catalyst;
   (c) from about 5 to about 99 percent by weight of liquid or supercritical carbon dioxide fluid; and
   (d) from zero to about 30 percent by weight of a cosolvent.

21. A mixture according to claim 20, wherein said carbon dioxide fluid comprises liquid carbon dioxide.

22. A mixture according to claim 20, wherein said carbon dioxide fluid comprises supercritical carbon dioxide.

23. A mixture according to claim 20, and having a pH of from about two to six.

24. A mixture according to claim 20, wherein said crosslinked enzyme crystal catalyst comprises an enzyme crystal crosslinked with a multifunctional crosslinking agent, said crosslinked enzyme crystal having resistance to exogeneous proteolysis, such that the crosslinked enzyme crystal retains at least about 80 percent of its initial activity after incubation for three hours in the presence of a concentration of Pronase™ protease that causes the soluble uncrosslinked form of the enzyme that is crystallized to form said enzyme crystal that is crosslinked to lose at least about 80 percent of its initial activity under the same conditions.

25. A mixture according to claim 20, wherein said crystal is a microcrystal.

26. A mixture according to claim 20, wherein said cosolvent comprises water.

27. A mixture according to claim 20, wherein said cosolvent comprises an organic cosolvent.

28. A method for the enzymatic production of a product in a liquid or supercritical carbon dioxide fluid, said method comprising:
   (a) providing a reaction mixture comprising at least one substrate and a crosslinked enzyme crystal catalyst in a liquid or supercritical carbon dioxide fluid; and
   (b) reacting said substrate with said crosslinked enzyme crystal catalyst in said carbon dioxide fluid to produce said product, wherein said reacting step is carried out as a transesterification reaction.

29. A method according to claim 28, wherein said carbon dioxide fluid comprises liquid carbon dioxide.

30. A method according to claim 28, wherein said carbon dioxide fluid comprises supercritical carbon dioxide.

31. A method according to claim 28, wherein said reaction mixture further comprises a cosolvent.

32. A method according to claim 28, wherein said reacting step is carried out at a pH of from about two to six.

33. A method according to claim 28, wherein said crosslinked enzyme crystal catalyst comprises an enzyme crystal crosslinked with a multifunctional crosslinking agent, said crosslinked enzyme crystal having resistance to exogeneous proteolysis, such that the crosslinked enzyme crystal retains at least about 80 percent of its initial activity after incubation for three hours in the presence of a concentration of Pronase™ protease that causes the soluble uncrosslinked form of the enzyme that is crystallized to form said enzyme crystal that is crosslinked to lose at least about 80 percent of its initial activity under the same conditions.

34. A method according to claim 28, wherein said crystal is a microcrystal.

35. A method according to claim 28, wherein said at least one substrate comprises sec-phenethyl alcohol and vinyl butyrate.

36. A method according to claim 28, wherein said product is soluble in said reaction mixture.

37. A method according to claim 28, wherein said product is insoluble in said reaction mixture.

38. A method according to claim 28, wherein said reacting step is followed by the step of:
   (c) separating said product from said reaction mixture.

39. A method according to claim 38, wherein said reacting step is carried out in a reaction vessel, and said separating step is carried out by venting said carbon dioxide from said reaction vessel.

40. A mixture useful for the enzymatic production of a product in carbon dioxide fluid, said mixture comprising:
   (a) from about 0.01 to about 50 percent by weight of at least one substrate comprising sec-phenethyl alcohol and vinyl butyrate;
   (b) from about 0.01 to about 50 percent by weight of a crosslinked enzyme crystal catalyst;
   (c) from about 5 to about 99 percent by weight of liquid or supercritical carbon dioxide fluid; and
   (d) from zero to about 30 percent by weight of a cosolvent.

41. A mixture according to claim 40, wherein said carbon dioxide fluid comprises liquid carbon dioxide.

42. A mixture according to claim 40, wherein said carbon dioxide fluid comprises supercritical carbon dioxide.

43. A mixture according to claim 40, and having a pH of from about two to six.

44. A mixture according to claim 40, wherein said crosslinked enzyme crystal catalyst comprises an enzyme crystal crosslinked with a multifunctional crosslinking agent, said crosslinked enzyme crystal having resistance to exogeneous proteolysis, such that the crosslinked enzyme crystal retains at least about 80 percent of its initial activity after incubation for three hours in the presence of a concentration of Pronase™ protease that causes the soluble uncrosslinked form of the enzyme that is crystallized to form said enzyme crystal that is crosslinked to lose at least about 80 percent of its initial activity under the same conditions.

45. A mixture according to claim 40, wherein said crystal is a microcrystal.

46. A mixture according to claim 40, wherein said cosolvent comprises water.

47. A mixture according to claim 40, wherein said cosolvent comprises an organic cosolvent.

48. A mixture produced from the catalytic action of an enzyme on a reaction substrate, said mixture comprising:
   (a) from about 0.01 to about 50 percent by weight of at least one reaction product formed from an esterification reaction;
   (b) from about 0.01 to about 50 percent by weight of a crosslinked enzyme crystal catalyst;
   (c) from about 5 to about 99 percent by weight of liquid or supercritical carbon dioxide fluid; and
   (d) from zero to about 30 percent by weight of a cosolvent.

49. A mixture according to claim 48, wherein said carbon dioxide fluid comprises liquid carbon dioxide.

50. A mixture according to claim 48, wherein said carbon dioxide fluid comprises supercritical carbon dioxide.

51. A mixture according to claim 48, and having a pH of from about two to six.

52. A mixture according to claim 48, wherein said crosslinked enzyme crystal catalyst comprises an enzyme crystal crosslinked with a multifunctional crosslinking agent, said crosslinked enzyme crystal having resistance to exogeneous proteolysis, such that the crosslinked enzyme crystal retains at least about 80 percent of its initial activity after incubation for three hours in the presence of a concentration of Pronase™ protease that causes the soluble uncrosslinked form of the enzyme that is crystallized to form said enzyme crystal that is crosslinked to lose at least about 80 percent of its initial activity under the same conditions.

53. A mixture according to claim 48, wherein said crystal is a microcrystal.

54. A mixture according to claim 48, wherein said cosolvent comprises water.

55. A mixture according to claim 48, wherein said cosolvent comprises an organic cosolvent.

* * * * *